(12) United States Patent
Kim et al.

(10) Patent No.: US 8,898,028 B2
(45) Date of Patent: Nov. 25, 2014

(54) NON-PATTERN WAFER INSPECTION DEVICE

(75) Inventors: Byeong-Cheol Kim, Hwaseong-si (KR);
Ho-Hyung Jung, Hwaseong-si (KR);
Dong-Keun Shin, Suwon-si (KR)

(73) Assignee: SAMSUNG Electronics Co., Ltd.,
Suwon-si (KR)

( * ) Notice: Subject to any disclaimer, the term of this patent is extended or adjusted under 35 U.S.C. 154(b) by 484 days.

(21) Appl. No.: 12/977,710

(22) Filed: Dec. 23, 2010

(65) Prior Publication Data
US 2011/0161014 A1 Jun. 30, 2011

(30) Foreign Application Priority Data
Dec. 28, 2009 (KR) .................. 10-2009-0131974

(51) Int. Cl.
*G01N 37/00* (2006.01)
*G01N 21/95* (2006.01)

(52) U.S. Cl.
CPC ........ *G01N 21/9501* (2013.01); *G01N 21/9503* (2013.01)
USPC ............... 702/81; 702/84; 702/155; 702/179; 702/185

(58) Field of Classification Search
USPC ............... 702/40, 172, 378, 81, 84, 155, 179, 702/185; 356/237, 237.2, 445; 250/491.1
See application file for complete search history.

(56) References Cited

U.S. PATENT DOCUMENTS 5,291,239 A * 3/1994 Jackson ................... 355/53
6,437,862 B1 * 8/2002 Miyazaki et al. ......... 356/237.2
6,863,732 B2 * 3/2005 Asano et al. ............... 118/715
7,190,458 B2 * 3/2007 Borden et al. ............. 356/445
7,280,200 B2 * 10/2007 Plemmons et al. ........ 356/237.3
7,884,948 B2 * 2/2011 Miyoshi et al. ............ 356/600

FOREIGN PATENT DOCUMENTS

| JP | 2000-124271 | 4/2000 |
| KR | 20050010667 | 1/2005 |
| KR | 20070069605 | 7/2007 |

OTHER PUBLICATIONS

Douglas C Montgomery, Introduction to Statistical Quality Control, 2005, John Wiley & Sons.*

* cited by examiner

*Primary Examiner* — Sujoy Kundu
*Assistant Examiner* — Harun Chowdhury
(74) *Attorney, Agent, or Firm* — Ellsworth IP Group PLLC

(57) ABSTRACT

A device to inspect a non-pattern wafer includes a light source to emit light that reflected from a wafer. A judgment unit converts the detected light into a quantitative measured value to determine whether the wafer is faulty. The wafer comprises a first region and a second region. The detection unit sequentially detects lights reflected from the first and second regions of the wafer, and a judgment unit converts the lights reflected from the first and second regions of the wafer into first and second quantitative measured values, respectively. The second region of the wafer is determined to be faulty by comparing the second measured value with a first reference value, wherein the first reference value is calculated using an average value between the first and second measured values, and a characteristic value that indicates distribution of the first and second measured values.

19 Claims, 11 Drawing Sheets

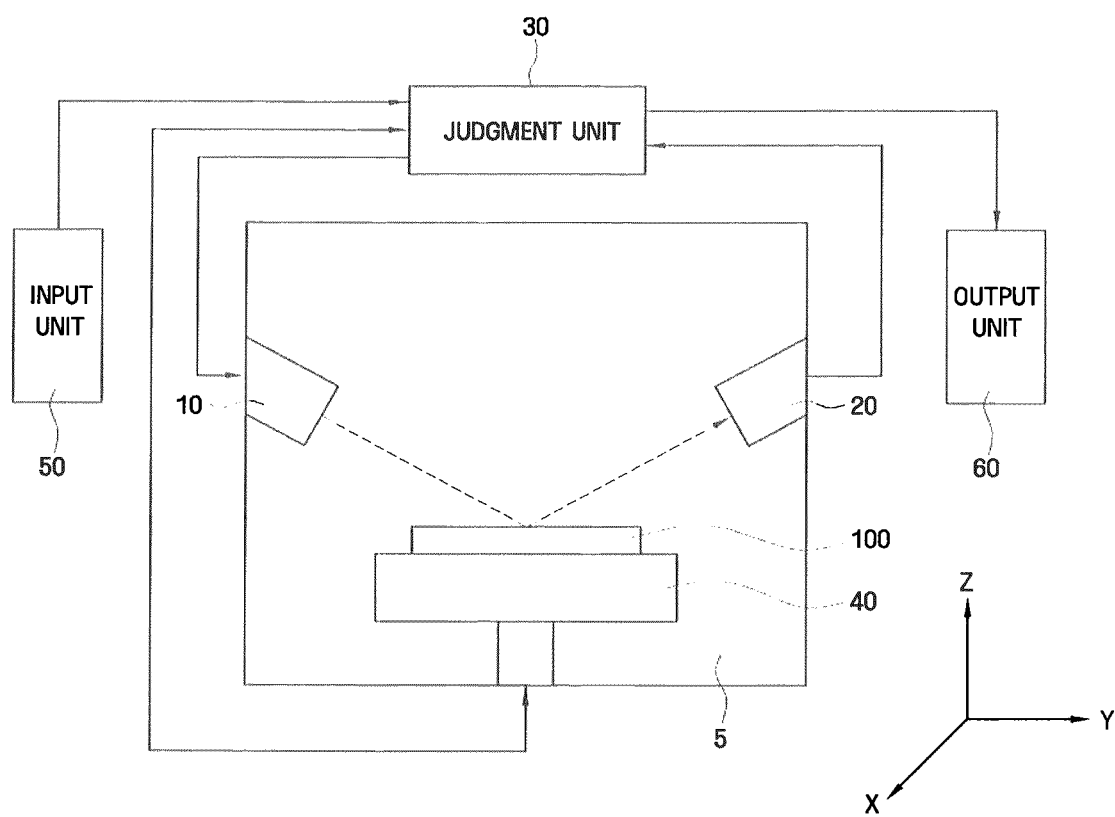

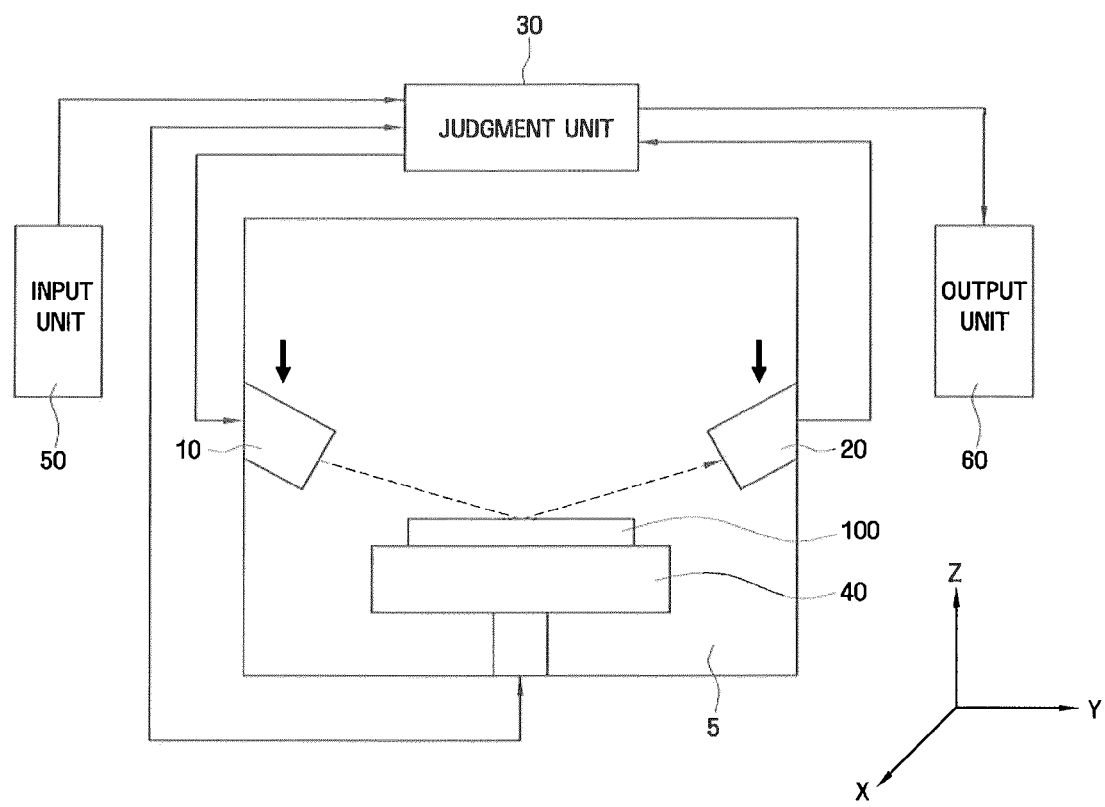

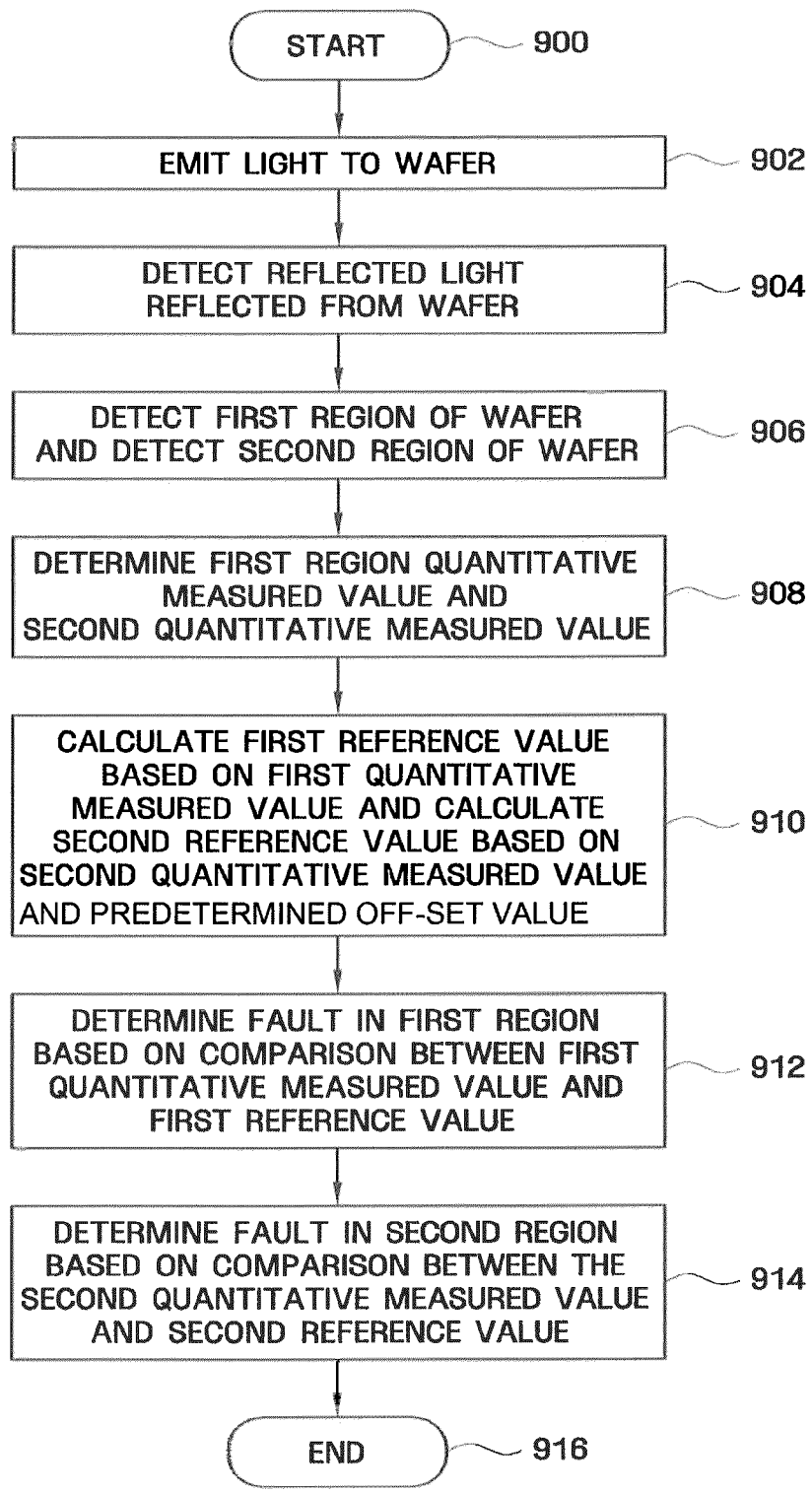

NON-PATTERN WAFER INSPECTION DEVICE

CROSS-REFERENCE TO RELATED APPLICATIONS

This application is based on and claims priority under 35 U.S.C. §119 from Korean Patent Application No. 10-2009-0131974, filed on Dec. 28, 2009 in the Korean Intellectual Property Office, the disclosure of which is incorporated herein in its entirety by reference.

BACKGROUND

1. Field of the Invention

The present inventive concept relates to a device to inspect a non-pattern wafer, and more particularly, to a device to inspect a non-pattern wafer that detects faults of a non-pattern wafer by applying different reference values to respective regions of the wafer.

2. Description of the Related Art

In general, a semiconductor device is formed by repeating processes of forming a plurality of layers on a wafer and patterning the layers. In this case, if faults, such as particle, voids, dislocations, and the like, which may occur in the process of forming the respective layers, exceeds a predetermined tolerance limit, a bad influence may be exerted upon the quality of a completed semiconductor device.

A device to inspect faults of a wafer so as to prevent in advance the occurrence of such faults is a wafer inspection device. A wafer inspection device may be classified into a pattern wafer inspection device to inspect a wafer on which a specified pattern is formed and a non-pattern wafer inspection device to inspect a wafer on which the specified pattern is not formed.

On the other hand, in a semiconductor process of forming a plurality of layers on a wafer, a layer formed on the wafer may have a non-uniform thickness due to the characteristics of semiconductor equipment, a local stepped portion formed thereon, and different surface roughness of respective regions of the wafer. Also, due to a high-temperature wafer processing, the wafer may get bent.

If the same reference value is applied to the whole regions of a wafer in inspecting a wafer having a local stepped portion formed thereon, a wafer having different surface roughness, or a bent wafer as described above, the fault inspection may be performed in a state where such local characteristics are not considered, and thus it is difficult to obtain a reliable result of inspection. This may cause the inferiority of products.

Accordingly, there is a need for a device to inspect faults of a non-pattern wafer in due consideration of the shape and characteristics of the plurality of layers formed on the wafer, and by using such a device, the reliability of the products can be improved.

SUMMARY

Accordingly, the present inventive concept has been made to solve the above-mentioned problems occurring in the prior art, and the subject to be solved by the inventive concept is to provide a device to inspect a non-pattern wafer that has an improved reliability.

Additional features and utilities of the present general inventive concept will be set forth in part in the description which follows and, in part, will be obvious from the description, or may be learned by practice of the present general inventive concept.

In order to accomplish the subject, in one feature of the present inventive concept, there is provided a device to inspect a non-pattern wafer, which comprises a light source emitting light; a detection unit detecting the light which is emitted from the light source and is reflected from a wafer; and a judgment unit converting the light detected by the detection unit into a quantitative measured value and determining whether the wafer is faulty based on the measured value; wherein the wafer comprises a first region and a second region, the detection unit sequentially detects lights reflected from the first and second regions of the wafer, and the judgment unit converts the lights reflected from the first and second regions of the wafer, which are sequentially detected by the detection unit, into first and second quantitative measured values, respectively, and determines whether the second region of the wafer is faulty by comparing the second measured value with a first reference value; wherein the first reference value is calculated using an average value between the first and second measured values and a characteristic value that indicates distribution of the first and second measured values.

In another feature of the present inventive concept, there is provided a device to inspect a non-pattern wafer, which comprises a light source emitting light; a detection unit detecting the light which is emitted from the light source and is reflected from a wafer that comprises first and second regions; a support unit supporting one surface of the wafer and being movable in a first direction; and a judgment unit converting the lights reflected from the first and second regions of the wafer, which are detected by the detection unit, into first and second quantitative measured values, respectively, determining whether the first region of the wafer is faulty by comparing the first measured value with a first reference value, and determining whether the second region of the wafer is faulty by comparing the second measured value with a second reference value; wherein the first reference value and the second reference value are different from each other, and if the first or second measured value escapes from a predetermined range, the judgment unit moves the support unit in the first direction so that the first or second measured value is within the predetermined range.

In still another feature of the present inventive concept, there is provided a device to inspect a non-pattern wafer, which comprises a light source emitting light; a detection unit detecting the light which is emitted from the light source and is reflected from a center region and an edge region of a wafer; a support unit supporting one surface of the wafer and being movable in one direction; and a judgment unit converting the light reflected from the center region of the wafer, which is detected by the detection unit, into a first quantitative measured value, determining whether the center region of the wafer is faulty by comparing the first measured value with a first reference value, converting the light reflected from the edge region of the wafer into a second quantitative measured value, and determining whether the edge region of the wafer is faulty by comparing the second measured value with a second reference value that is different from the first reference value; wherein the first reference value is calculated as a sum of an average between the measured values, which have already been converted by the judgment unit, and the first measured value and a standard deviation between the measured values, which have already been converted, and the first measured value, which is multiplied by a predetermined coefficient; the second reference value is calculated by adding a predetermined offset value to the first reference value; and if the first or second measured value escapes from a predetermined range, the judgment unit moves the support unit in one direction so that the first or second measured value is within the predetermined range.

In another feature of the present general inventive concept, a method of inspecting a non-pattern wafer comprises emitting light to a surface region of the wafer to reflect the emitted light therefrom, detecting a first region of the wafer and a second region of the wafer different from the first region based on reflected light from the wafer, determining a first quantitative measured value corresponding to light reflected by the first region and detecting a second quantitative measured value corresponding to light reflected by the second region, calculating a first reference value based on the first quantitative measured value and calculating a second reference value based on the second quantitative measured value and a predetermined offset value, and determining a fault in the first region based on a comparison between the first quantitative measured value and the first reference value and determining a fault in the second region based on a comparison between the second quantitative measured value and the second reference value.

In yet another feature of the present general inventive concept, a device to inspect a non-pattern wafer comprises a light source to emit light to a surface of the wafer, a detection unit to detect a first region of the wafer based on reflected light reflected from the first region and an adjacent region of the wafer different from the first region based on reflected light reflected from the second region, and a judgment unit to determine an adjacent quantitative measured value corresponding to reflected light reflected by the adjacent region and to determine an adjacent reference value based on the adjacent quantitative measured value and a predetermined offset value and to determine a fault in the adjacent region based on a comparison between the adjacent quantitative measured value and the adjacent reference value.

In still another feature of the present general inventive concept, a device to inspect a non-pattern wafer comprises a support unit supporting a surface of the wafer having first and second regions, a light source moveably disposed adjacent the support unit to move along an inspection path about the wafer to emit light to at least one of the first and second regions, a detection unit moveably disposed adjacent the support unit opposite the light source to move along the inspection path parallel with the light source to detect the light emitted from the light source and reflected from the at least first and second regions, and a judgment unit to convert detected light reflected from the at least first and second regions of the wafer into first and second quantitative measured values, respectively, to determine whether the first region of the wafer is faulty by comparing the first measured value with a first reference value, and to determine whether the second region of the wafer is faulty by comparing the second measured value with a second reference value, wherein the first reference value and the second reference value are different from each other, and when the first or second measured value escapes from a predetermined range, the judgment unit controls the movement of at least one of the light source and the detection unit in the at least first direction so that at least one of the first measured value and second measured value is within the predetermined range.

BRIEF DESCRIPTION OF THE DRAWINGS

The above and/or other features of the present general inventive concept will become apparent and more readily appreciated from the following description of the exemplary embodiments, taken in conjunction with the accompanying drawings, in which:

FIGS. 1A-1C are a schematic views illustrating a device to inspect a non-pattern wafer according to an exemplary embodiment of the present inventive concept;

FIG. 9 is a flow diagram illustrating a method of inspecting a non-pattern wafer according to an exemplary embodiment of the present inventive concept.

DETAILED DESCRIPTION OF THE EMBODIMENTS

Figure 1B:
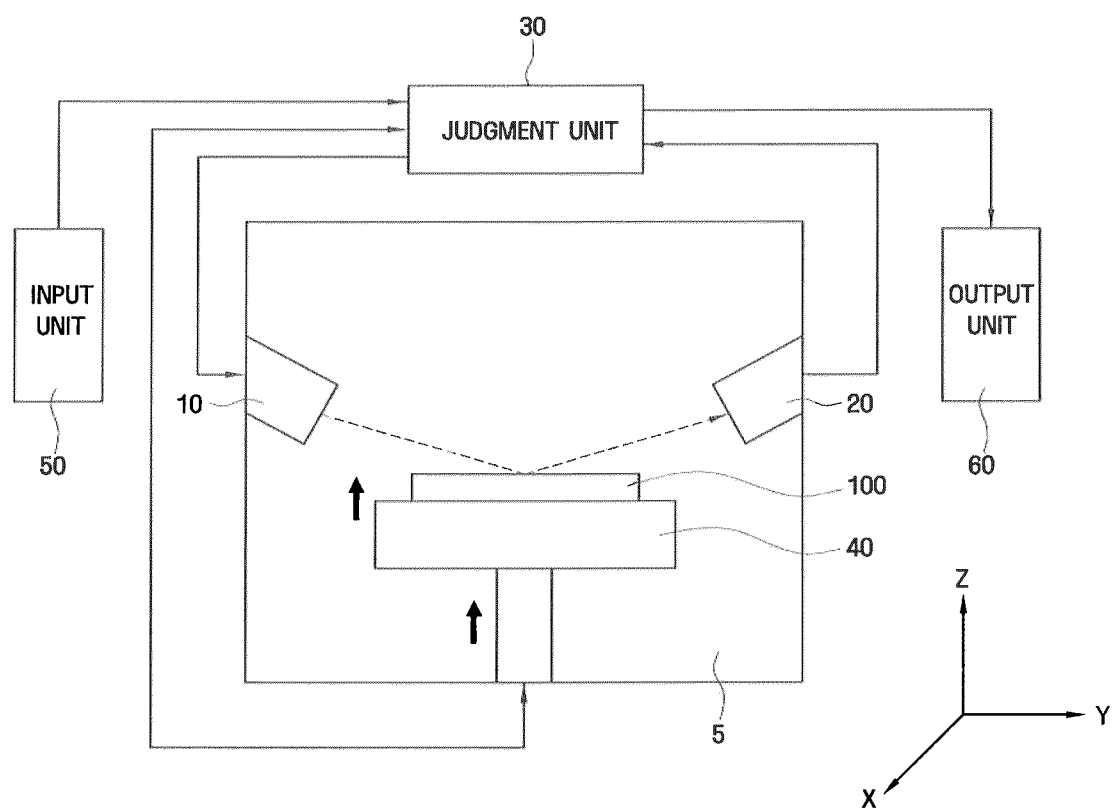

Reference will now be made in detail to the exemplary embodiments of the present general inventive concept, examples of which are illustrated in the accompanying drawings, wherein like reference numerals refer to the like elements throughout. The exemplary embodiments are described below in order to explain the present general inventive concept by referring to the figures. The features of the present inventive concept and methods to achieve the features will be apparent by referring to the exemplary embodiments to be described in detail with reference to the accompanying drawings. However, the present inventive concept is not limited to the exemplary embodiments disclosed hereinafter, but can be implemented in diverse forms. The matters defined in the description, such as the detailed construction and elements, are nothing but specific details provided to assist those of ordinary skill in the art in a comprehensive understanding of the inventive concept, and the present inventive concept is only defined within the scope of the appended claims. In some exemplary embodiments of the present inventive concept, well-known element structures and technologies are not described in detail since they would obscure the inventive concept in unnecessary detail.

Although the terms "first, second, and so forth" are used to describe diverse elements, components and/or sections, such elements, components and/or sections are not limited by the terms. The terms are used only to discriminate an element, component, or section from other elements, components, or sections. Accordingly, in the following description, a first element, first component, or first section may be different from or may be identical to a second element, second component, or second section.

Unless specially defined, all terms (including technical and scientific terms) used in the description could be used as meanings commonly understood by those ordinary skilled in the art to which the present inventive concept belongs. In addition, terms that are generally used but are not defined in the dictionary are not interpreted ideally or excessively unless they have been clearly and specially defined.

Hereinafter, with reference to FIGS. 1 to 6, a device to inspect a non-pattern wafer according to an embodiment of the present inventive concept will be described.

Figure 2:
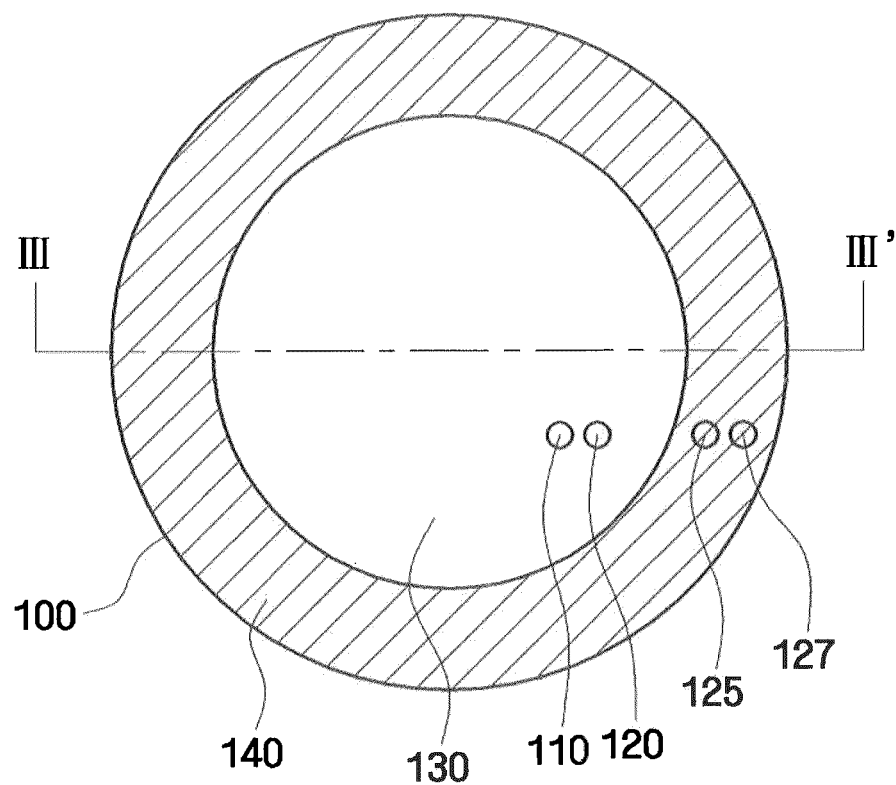
FIG. 2 is a plan view illustrating wafer region division of a device to inspect a non-pattern wafer according to an exemplary embodiment of the present inventive concept.
Figure 3:
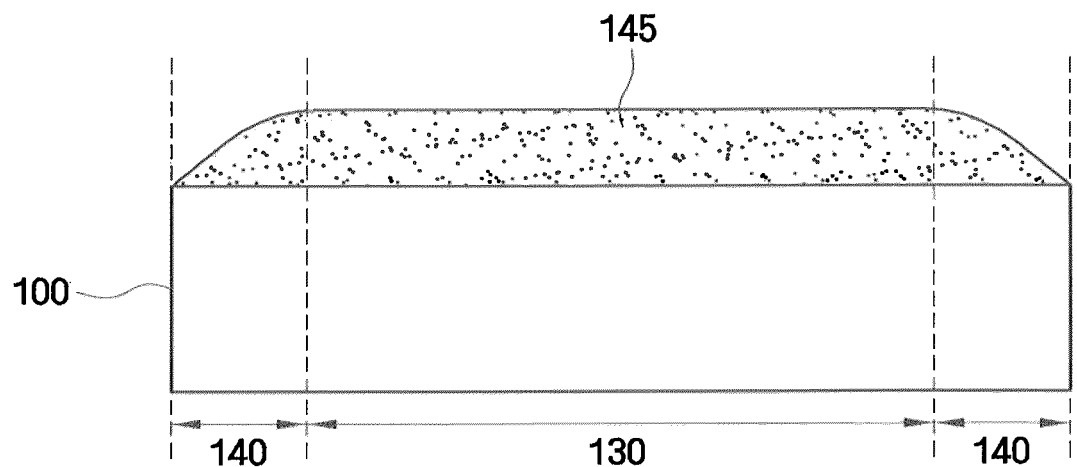
FIG. 3 is a sectional view taken along line III-III' in FIG. 2.
Figure 4:
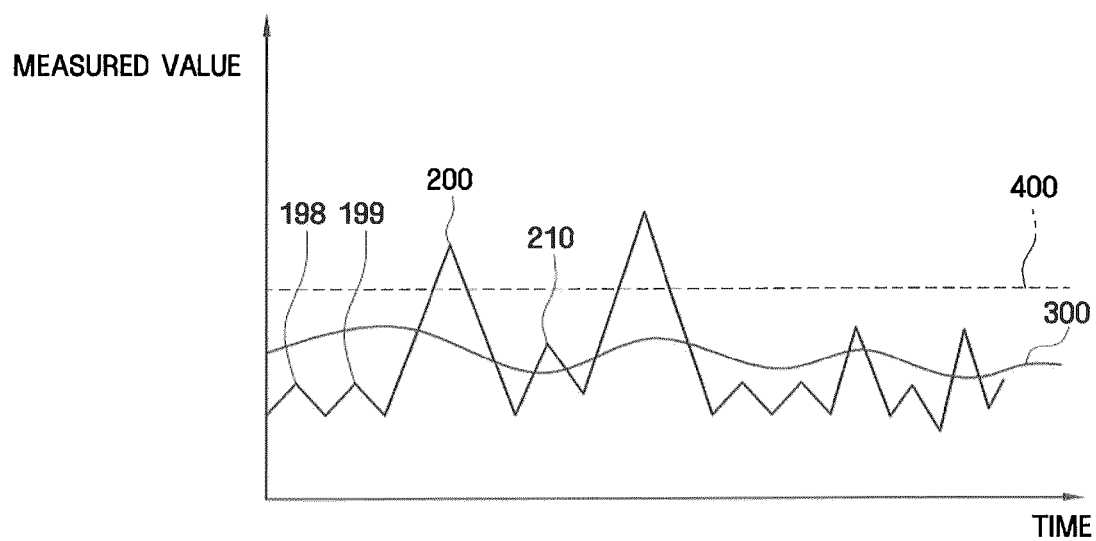
FIGS. 4 and 5 are views illustrating reference values of a device to inspect a non-pattern wafer according to an exemplary embodiment of the present inventive concept.
Figure 5:
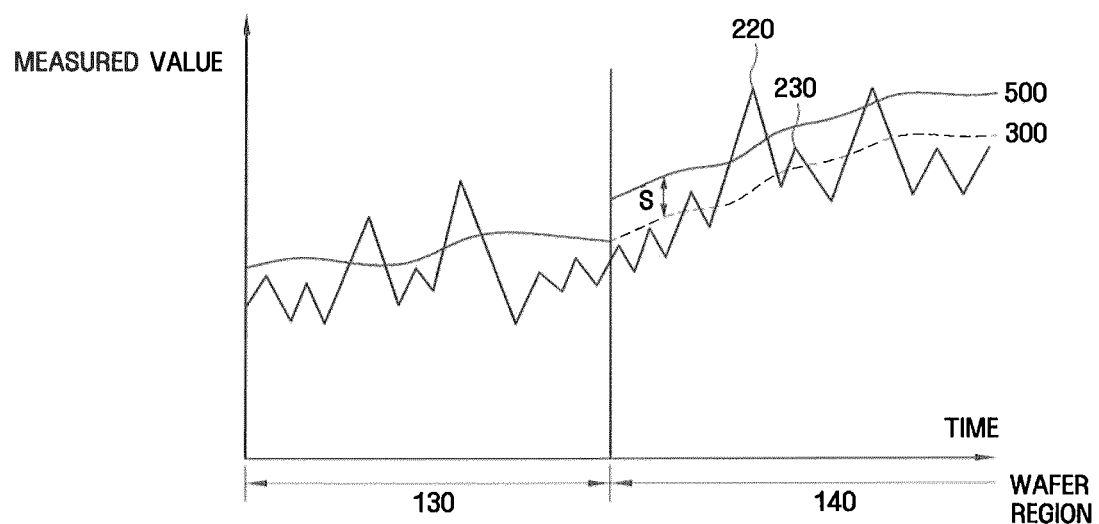
Figure 6:
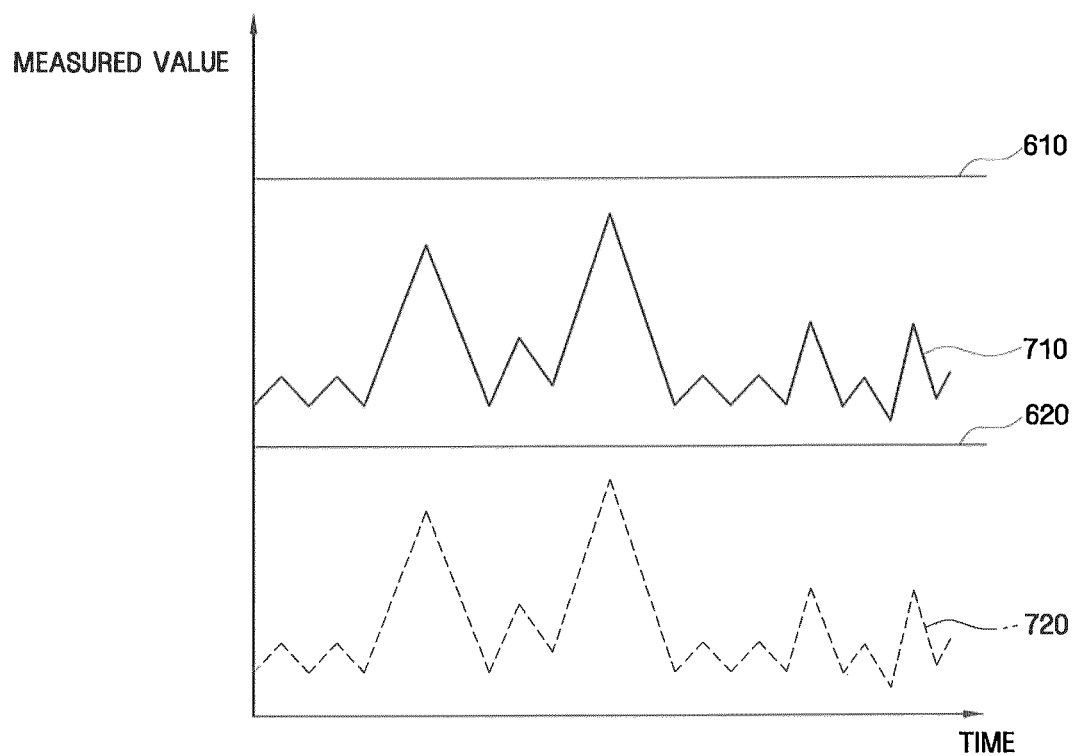
FIG. 6 is a view illustrating an operation of a support unit of a device to inspect a non-patent wafer according to an exemplary embodiment of the present inventive concept.

FIG. 1 is a schematic view explaining a device to inspect a non-pattern wafer according to an exemplary embodiment of the present inventive concept. FIG. 2 is a plan view explaining wafer region division of a device to inspect a non-pattern wafer according to an embodiment of the present inventive concept, and FIG. 3 is a sectional view taken along line III-III' in FIG. 2. FIGS. 4 and 5 are views explaining reference values of a device to inspect a non-pattern wafer according to an embodiment of the present inventive concept, and FIG. 6 is a view explaining an operation of a support unit of a device to inspect a non-patent wafer according to an embodiment of the present inventive concept.

First, referring to FIG. 1, the device to inspect a non-pattern wafer according to an exemplary embodiment of the present inventive concept may comprise a light source 10, a detection unit 20, a judgment unit 30, a support unit 40, an input unit 50 that may be manipulated by a user, and an output unit 60 to display results of an inspected wafer to the user.

The light source 10 may be a unit that emits light. Specifically, the light source 10 may be a unit which emits light to a specified position of a surface of a wafer 100 that is in an inspection standby state within an inspection space 5 at a predetermined incident angle. Such light includes, but is not limited to, a laser light. However, this is merely exemplary, and the present inventive concept is not limited thereto.

The detection unit 20 may be a unit that detects the light that is emitted from the light source 10 and is reflected from the wafer 100. Specifically, the detection unit 20 may be a unit that detects the light that is reflected from the specified position on the surface of the wafer 100 at a predetermined reflection angle. Here, the light source 10, the wafer 100, and the detection unit 20 may be positioned within the same inspection space 5 as illustrated in FIG. 1. Further, the detection unit 20 may be in communication with the judgment unit 30. In response to detecting the reflected light, the detection unit may output a detection signal to the judgment unit 30 indicative of the region of the wafer reflecting the light. Accordingly, the judgment unit 30 receives the detection signal may determine the region of the wafer to be inspected.

The light source 10 and the detection unit 20 may be positioned opposite one another on the same plane. The wafer 100 has one surface that is fixed to the support unit 40 such that the wafer remains stationary. The light source 10 and the detection unit 20 may move about the wafer at the same speed in a first direction X or a second direction Y to inspect the whole region of the wafer 100. In contrast, the light source 10 and the detection unit 20 may be stationary, and the support unit 40 may move in the first direction X or the second direction Y, which travels along a predetermined detection path. One surface of he wafer is fixed to the support unit 40 such that the wafer moves together with the support unit 40. As the support moves along the detection path, the light source 10 and the detection unit 20 inspect the whole region of the wafer 100.

The judgment unit 30 may be a unit which converts the light detected by the detection unit 20 into a quantitative measured value, and determines whether the wafer 100 is faulty based on the measured value, as discussed in greater detail below. More specifically, the judgment unit 30 may convert the light detected by the detection unit 20 into, for example, a quantitative measured value, such as light intensity, and determines whether the wafer 100 is faulty by comparing the converted measured value with a reference value, as discussed further below. Here, the fault of the wafer 100 may include, but is not limited to, a particle, a void, a dislocation, a stacking fault, an interface fault, and the like.

Hereinafter, with reference to FIGS. 2 to 5, the judgment unit 30 of the device to inspect a non-pattern wafer according to an exemplary embodiment of the present inventive concept will be described in more detail.

First, referring to FIG. 2, the wafer 100 may comprise a center region 130 and an edge region 140. The center region 130, as illustrated in FIG. 2, may include the middle and peripheral region of the wafer 100, and the edge region 140 may include the border of the wafer 100.

Referring now to FIG. 3, a layer 145 deposited on the center region 130 of the wafer 100 may be thicker than the layer 145 deposited on the edge region 140 of the wafer 100 due to the characteristics of deposition equipment and deposition processes. Accordingly, the thickness of the center region 130 of the wafer in consideration of the thickness of the layer 145 may be larger than the thickness of the edge region 140.

Accordingly, a method of determining whether the center region 130 of the wafer 100 is faulty and a method of determining whether the edge region 140 of the wafer 100 is faulty, which are performed by the judgment unit 30, will be described in order.

Referring to FIGS. 1, 2, and 4, if the detection unit 20 detects the light reflected from a first region 110 located in the center region 130 of the wafer 100, the judgment unit 30 converts the detected light into a first quantitative measured value 200, such as light intensity. Then, the judgment unit 30 compares the first measured value 200 with a first variable reference value 300 that may be stored in a memory of the judgment unit 30. If the first measured value 200 is larger than the first variable reference value 300, the judgment unit 30 may determine that the first region 110 of the wafer 100 is faulty.

Here, the first variable reference value 300 of the center region 130 may be calculated by the judgment unit 30 using the following Equation (1):

$$\text{First variable reference value} = \text{average value} + K*\sigma \quad (1)$$

Here, the average value may be an average value between the previously measured values 198 and 199, which have been previously converted by the judgment unit 30, and the first measured value 200. Although an exemplary embodiment illustrated in FIG. 4 shows only two previously measured values 198 and 199, which have been previously converted by the judgment unit 30, more previously measured values, which have been previously converted by the judgment unit 30, may be provided. That is, the average value may be an accumulated average value between a plurality of previously measured values, which have been already previously converted by the judgment unit 30, and the first measured value 200.

"K" may be a predetermined coefficient which may be input by a user through the input unit 50.

The value "σ" may be a characteristic value, for example, a standard deviation value, calculated by the judgment unit 30 and stored therein to be utilized to determine the first variation reference value. More specifically, the value "σ" indicates the distribution of the measured values 198 and 199, which have already been converted by the judgment unit 30, and the first measured value 200. It can be appreciated that additional measured values than those illustrated in FIG. 4, which have already been converted by the judgment unit 30, may be provided.

The first variation reference value 300, as determined above, is compared with the first measured value 200. If the first measured value 200 is greater than the first variable reference value 300, the judgment unit 30 determines that the first region 110 of the wafer 100 is faulty.

However, if the detection unit 20 detects that the reflected light is reflected from the second region 120 located in the center region 130 of the wafer 100, the judgment unit 30 converts the detected light into a second quantitative measured value 210. Accordingly, the judgment unit 30 compares the second measured value 210 with the first variable reference value 300 determined according to Equation (1) described above. If the second measured value 210 is greater then the first variable reference value 300, the judgment unit 30 determines that the second region 120 of the wafer 100 is faulty.

Here, the average value used to calculate the first variable reference value 300 may be an average value between the measured values 198, 199, and 200, which have been previously converted by the judgment unit 30, and the second measured value 210. Further, the value, "σ" may be a predetermined characteristic value (e.g. standard deviation value) stored in the judgment unit 30 that indicates the distribution of the measured values 198, 199, and 200, which have been previously converted by the judgment unit 30, and the second measured value 210.

Referring to FIG. 4, in the case where the first variable reference value 300 is calculated and compared with the measured values 200 and 210, it is possible to perform a more reliable fault inspection of the wafer 100. More specifically, if it is assumed that the fault exists in the second region 120 of the wafer 100 and the measured value based on light reflected from the wafer is small due to the influence of stepped portions of the surface of the wafer 100 or the like, a predetermined fixed reference value 400 stored in the judgment unit 30 and the second measured value 210 are compared with each other rather than comparing the first variable reference value 300 with the second measured value 210. In this case, as illustrated in FIG. 4, the judgment unit 30 may determine that the second region 120 of the wafer 100 is not faulty.

Referring now to FIGS. 1, 2, and 5, if the detection unit 20 detects that the reflected light is reflected from a third region 125 located in the edge region 140 of the wafer 100, the judgment unit 30 converts the detected light into a third quantitative measured value 220. Accordingly, the judgment unit 30 compares the third measured value 220 with a second variable reference value 500. If the third measured value 220 is larger then the second variable reference value 500, the judgment unit 30 determines that the third region 125 located in the edge region 140 of the wafer 100 is faulty.

Here, the judgment unit 30 may calculate the second variable reference value 500 of the edge region 140 based on the following Equation (2):

$$\text{Second variable reference value} = \text{average value} + K^*\sigma + S \quad (2)$$

Here, since the average value, K, and σ are the same as those as described above, the duplicate explanation thereof will be omitted. The value "S" is a predetermined offset value, and may be a value input by a user through the input unit 50, and may be a value that offsets difference in thickness between the first region and the second region. That is, the offset value "S" may be a value that offsets a difference in thickness between a layer 145 deposited on the center region 130 of the wafer 100 and the layer 145 deposited on the edge region 140 of the wafer 100. Although FIG. 5 illustrates an offset value S having a positive value, the present inventive concept is not limited thereto, and the offset value S may have a negative value as needed. Accordingly, an inconsistency between two regions of the wafer 100, for example, a thickness differential between a layer 145 located at a center region 130 and the layer 145 located at an edge region 140 may be taken into account. Therefore, a more reliable inspection of the wafer 100 may be performed, as discussed in greater detail below.

The second variation reference value 500, as determined according to Equation (2) above, is compared with the third measured value 220. If the third measured value 220 is larger than the second variable reference value 500, it is judged that the third region 220 of the wafer 100 is faulty.

Then, if the detection unit 20 detects the light that is reflected from a fourth region 127 located in the edge region 140 of the remaining wafer 100, the judgment unit 30 converts the detected light into a fourth quantitative measured value 230, and compares the fourth measured value 230 with the second variable reference value 500. If the fourth measured value 230 is larger then the second variable reference value 500, the judgment unit 30 determines that the fourth region 127 located in the edge region 140 of the wafer 100 is faulty in the same manner as described above.

Referring to FIG. 5, in the case where the second variable reference value 500 is calculated by adding the predetermined offset value S to the first variable reference value 300, and the second variable reference value 500 is compared with the measured values 220 and 230, it is possible to perform the fault inspection of the wafer 100 more reliably. Specifically, if it is assumed that the fault does not exist in the fourth region 127 of the wafer 100, but the measured value is large due to the influence of the stepped portions of the surface of the wafer 100 or the like, the fourth measured reference value 230 is compared to the first variable reference value 300, rather than comparing the fourth measured reference value 230 to second variable reference value 500. Accordingly, as illustrated in FIG. 5, the judgment unit 30 may determine that the fourth region 127 of the wafer 100 is faulty.

Although it is exemplified in FIGS. 2 and 3 that the thicknesses of the center region 130 and the edge region 140 of the wafer 100 are different from each other, the thicknesses of the center region 130 and the edge region 140 of the wafer 100 may be the same, but their surface roughness may differ. That is, even with respect to the center region 130 and the edge region 140 of the wafer 100 having the same thickness and different surface roughness, it may be possible to perform the fault measurement of the wafer 100 by the above-described method.

Referring now to FIGS. 1A and 1B, the support unit 40 may be a unit which supports one surface of the wafer 100. Further, the support unit is in communication with the judgment unit 30 and is movable in at least one direction (e.g. in a direction (Z)) based on a position signal output by the judgment unit 30. Specifically, the support unit 40 may be a unit which supports one surface of the wafer 100 and moves in at least one direction (e.g. in the direction (Z)), under the control of the judgment unit 30, to adjust a reflection angle of the light reflected from the wafer 100.

As illustrated in FIG. 6, when the detection unit 20 detects the light reflected from the wafer 100, the judgment unit 30 converts the detected light into a quantitative measured value. If the measured value is a measured value 720 that is beyond a range having an upper limit value 610 and a lower limit value 620, the judgment unit 30 outputs the position signal to move the support unit 40 in at least one direction (e.g. in the direction (Z)), so that the measured value becomes the measured value 710 that is within the range between the upper limit value 610 and the lower limit value 620, as shown in FIG. 1B. Here, the upper limit value 610 and the lower limit value 620 may be values input by a user through the input unit 50 illustrated in FIG. 1.

If the judgment unit 30 moves the support unit 40 in the at least one direction (e.g. in the direction (Z)) and the measured value is determined to exist within the predetermined range between the upper limit value 610 and the lower limit value 620, the stepped portions, for example, on the surface of the wafer 100 can be automatically considered. Therefore, a more reliable fault inspection of the wafer 100 becomes possible.

In an alternative embodiment illustrated in FIG. 1C, the support unit 40 may be fixed to support the wafer 100 in a fixed position, while the light source 10 and the detection unit 20 move about the support unit in at least one direction (e.g. in a direction (Z)). More specifically, the both the light source 10 and the detection unit 20 are in communication with the judgment unit 30. The judgment unit 30 outputs a position signal to move the light source 10 and the detection unit 20 based on a measured value and a predetermined judgment range. For example, when the detection unit 20 detects the light reflected from the wafer 100, the judgment unit 30 converts the detected light into a quantitative measured value. If the measured value is a measured value 720 that outside a range having an upper limit value 610 and a lower limit value 620, the judgment unit 30 outputs a position signal to move at least one of the light source 10 and the detection unit 20 in at least one direction (e.g. in the direction (Z)), as illustrated in FIG. 1C. Alternatively, both the light source 10 and the detection unit 20 may be moved in parallel with each other until the measured value 720 falls within the range. Accordingly, the measured value becomes the measured value 710 that is within the range between the upper limit value 610 and the lower limit value 620. Here, the upper limit value 610 and the lower limit value 620 may be values input by a user through the input unit 50.

Referring again to FIG. 1, the input unit 50 may receive an input command from a user and may output the input command to the judgment unit 30. As described above, a user can utilize the input unit 50 to input an input command such as the average value K, the offset value S, the upper limit value 610, the lower limit value 620, and the like, to allow the judgment unit 30 to determine whether a fault exists in the wafer 100. The output unit 60 may be a unit which outputs, i.e., displays, an inspection result, such as the measured value that is converted by the judgment unit 30, whether the wafer 100 is faulty, and/or the like, to the user.

Figure 7:
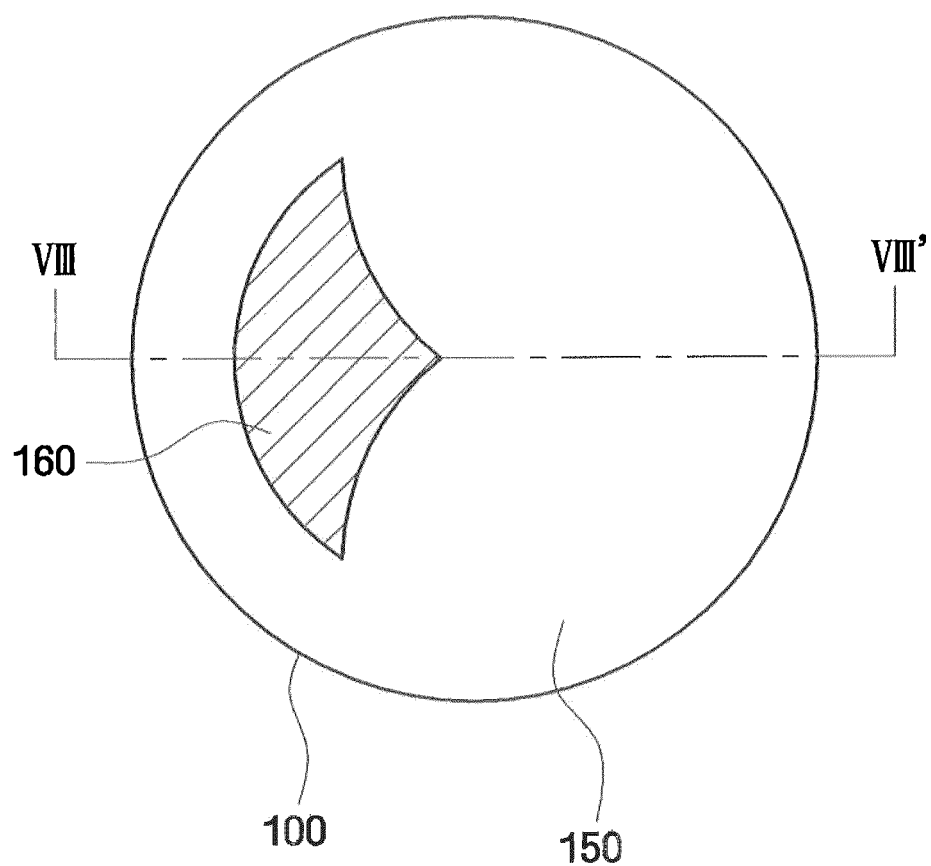
FIG. 7 is a plan view illustrating wafer region division of a device to inspect a non-pattern wafer according to another exemplary embodiment of the present inventive concept.
Figure 8:
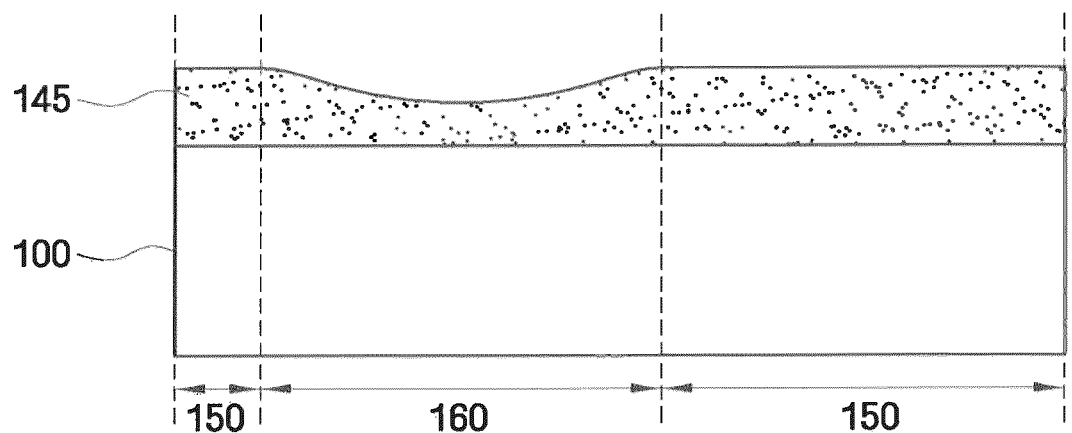
FIG. 8 is a sectional view taken along line VIII-VIII' in FIG. 7.

Referring now to FIGS. 7 and 8, a device to inspect a non-pattern wafer according to another embodiment of the present inventive concept will be described.

FIG. 7 is a plain view illustrating a wafer region division of a device to inspect a non-pattern wafer according to another exemplary embodiment of the present inventive concept. FIG. 8 is a sectional view taken along line VIII-VIII' of FIG. 7.

Since the construction and operation of the device to inspect a non-pattern wafer according to another embodiment of the present inventive concept are the same as those of the device to inspect a non-pattern wafer according to an embodiment of the present inventive concept, the duplicate detailed explanation thereof will be omitted.

Referring to FIG. 7, the wafer 100 may comprise a basic region 150 and a masking region 160. That is, in the case of the device to inspect a non-pattern wafer according to an exemplary embodiment of the present inventive concept as described above, the wafer 100 is divided into the center region 130 and the edge region 140. However, in the alternative exemplary embodiment illustrated in FIG. 7, the wafer 100 is divided into the basic region 150 and the masking region 160.

On the other hand, FIG. 8 illustrates a deposit layer 145 deposited on the basic region 150. In this case, the deposit layer 145 located in the basic regions may be thicker than the deposit layer 145 located in the masking region due to the characteristics of deposition equipment and deposition processes. Accordingly, the thickness of the basic region 150 of the wafer 100 in consideration of the thickness of the layer 145 may be larger than the thickness of the masking region 160.

In another exemplary embodiment of the present inventive concept, the method of inspecting the basic region 150 and the masking region 160 of the wafer 100 is similar to the method of inspecting a non-pattern wafer according to an embodiment of the present inventive concept as described above. The judgment unit 30 may determine the area of the wafer 100 comprising the basic region 150 and the area of the region comprising the masking region 160, as described further below. However, an offset value S is additionally considered when the judgment unit 30 determines whether the masking region 160 of the wafer 100 is faulty, as opposed to determining whether the basic region 150 of the wafer 100 is faulty.

Although FIG. 7 illustrates the masking region 160 of the wafer 100 as being formed in a fan shape, the present inventive concept is not limited thereto, and the masking region 160 of the wafer 100 may be an arbitrary region on the wafer 100. Specifically, in a device to inspect a non-pattern wafer according to another exemplary embodiment of the present inventive concept, the masking region 160 of the wafer 100 may be an arbitrary region of the wafer 100 which is designated by a user through the input unit 50 shown in FIG. 1, and the user designation is output from the input unit 50 to the judgment unit 30. That is, the user can designate the masking region through an input device including, but not limited to, a mouse, a keyboard, and the like, so that the offset value S is reflected in the region in consideration of the thickness of the wafer 100. Accordingly, the judgment unit 30 may determine the area comprising the basic region 150 and the masking region 160. Although it is exemplified in FIG. 8 that the thicknesses of the basic region 150 and the masking region 160 are different from each other, regions having different surface roughness may be designated as the basic region 150 and the masking region 160.

Referring now to FIG. 9, a flowchart is shown illustrating an exemplary method of inspecting a non-pattern wafer according to the general inventive concept. The method begins at operation 900 and proceeds to operation 902 where light from a light source 10 is emitted to a surface of a wafer 100. The wafer 100 reflects the light, and the reflected light is detected by the detection unit 20 in operation 904. In operation 906, at least one of a first region of the wafer and a second region of the wafer is detected based on the detected reflected light. In operation 908, a first quantitative measured value and a second quantitative measured value corresponding to first and second regions, respectively, may be determined by the judgment unit 30 based on a detection signal output by the detection unit 30 indicative of the reflected light. In operation 910, first and second reference values may be calculated. More specifically, a first reference value may be calculated by the judgment unit 30 based on the first quantitative measured value, and a second reference value may be calculated by the judgment unit 30 based on the second quantitative measured value and an offset value (S). As discussed above, the offset value may be a value that takes into account inconsistencies between a first region of the wafer and a second region of the wafer, for example, a thickness differential in a layer 145 located in a first region and the layer 145 located in the second region. Accordingly, in operation 912, it may be determined whether a fault exits in the first region based on a comparison between the first quantitative measured value and the first reference value. In operation 914, a it may be determined whether a fault exists in the second region based on a comparison between the second quantitative measured value and the second reference value, and the inspection method ends at operation 916.

As described above, a user may designate an arbitrary region on the wafer 100 in accordance with various kinds of characteristics of the wafer 100, including, but not limited to, the thickness, surface roughness, etc., and may perform a fault inspection by inputting different reference values to be compared against measured values of the respective regions. Accordingly, a more reliable fault inspection of the wafer 100 may be achieved.

Although a few embodiments of the present general inventive concept have been shown and described, it would be appreciated by those skilled in the art that changes may be made in these embodiments without departing from the principles and spirit of the general inventive concept, the scope of which is defined in the claims and their equivalents.

What is claimed is:

1. A device to inspect a non-pattern wafer comprising:
a light source emitting light;
a detection unit detecting the light that is emitted from the light source and is reflected from a wafer;
a judgment unit to convert the light detected by the detection unit into a quantitative measured value and to determine whether the wafer is faulty based on the measured value; and
a support unit to support one surface of the wafer and being movable in a vertical direction;
wherein the wafer comprises a first region and a second region;
the detection unit sequentially detects lights reflected from the first and second regions of the wafer; and
the judgment unit converts the lights reflected from the first and second regions of the wafer that are sequentially detected by the detection unit into first and second quantitative measured values, respectively, and determines whether the second region of the wafer is faulty by comparing the second measured value with a first reference value;
wherein the first reference value is calculated using an average value based on the first and second measured values and a characteristic value stored in the judgment unit that indicates a distribution of the first and second measured values; and
wherein when at least one of the first and second measured values escapes from a predetermined range, the judgment unit moves the support unit in the vertical direction so that the at least one of the first or second measured value is within the predetermined range.

2. The device of claim 1, wherein:
the characteristic value that indicates the distribution of the first and second measured values comprises standard deviation values of the first and second measured values; and
the reference value is a sum of the average value and a value based on a product of the standard deviation value and a predetermined coefficient.

3. The device of claim 2, further comprising an input unit receiving a command from a user and providing the input command to the judgment unit,
wherein the predetermined coefficient is a value input by a user through the command.

4. The device of claim 1, wherein the judgment unit determines that the second region of the wafer is faulty when the second measured value is larger than the first reference value.

5. The device of claim 1, wherein:
the wafer further comprises a third region; and
the judgment unit determines whether the third region of the wafer is faulty by converting the light reflected from the third region of the wafer, which is detected by the detection unit, into a third quantitative measured value, and comparing the third measured value with a second reference value that is obtained by adding an offset value to the first reference value.

6. The device of claim 5, wherein:
the first and second regions comprise a center region of the wafer; and
the third region comprises an edge region of the wafer.

7. The device of claim 5, wherein a first thickness that is a wafer thickness of the first and second regions is different from a second thickness that is a wafer thickness of the third region.

8. The device of claim 7, wherein the second thickness is smaller than the first thickness.

9. The device of claim 5, wherein a first surface roughness that is a wafer surface roughness of the first and second regions is different from a second surface roughness that is a wafer surface roughness of the third region.

10. The device of claim 5, further comprising an input unit to receive a command from a user and to provide the input command to the judgment unit,
wherein the offset value is a value input by a user through the command.

11. The device of claim 10, wherein the third region is an arbitrary region of the wafer that is designated by the user.

12. The device of claim 5, wherein the offset value has a positive value.

13. The device of claim 1, further comprising an input unit to receive a command from a user and to provide the input command to the judgment unit;
wherein the predetermined range is defined by an upper limit value and a lower limit value input by the user through the command.

14. A device to inspect a non-pattern wafer comprising:
a light source emitting light;
a detection unit detecting the light that is emitted from the light source and that is reflected from a wafer that comprises first and second regions;
a support unit supporting one surface of the wafer and being movable in a vertical direction; and
a judgment unit to convert the lights reflected from the first and second regions of the wafer and detected by the detection unit, into first and second quantitative measured values, respectively, to determine whether the first region of the wafer is faulty by comparing the first measured value with a first reference value, and to determine whether the second region of the wafer is faulty by comparing the second measured value with a second reference value;
wherein the first reference value and the second reference value are different from each other; and
when the first or second measured value escapes from a predetermined range, the judgment unit moves the support unit in the vertical direction so that at least one of the first measured value and second measured value is within the predetermined range.

15. The device of claim 14, wherein:
the light source emits the light to the first or second region of the wafer as the light source moves in a second direction that is perpendicular to the first direction; and
the detection unit detects the light reflected from at least one of the first region and the second region of the wafer as the detection unit moves in the second direction.

16. The device of claim 15, wherein:
a moving speed of the light source is equal to a moving speed of the detection unit.

17. The device of claim 14, wherein the first region comprises a center region of the wafer; and
the second comprises an edge region of the wafer.

18. The device of claim 14, further comprising an input unit to receive a command from a user and to provide the input command to the judgment unit,
wherein the second region is a region of the wafer that is designated by the user through the command.

19. A device to inspect a non-pattern wafer comprising:
a light source emitting light;
a detection unit detecting the light that is emitted from the light source and that is reflected from a center region and an edge region of a wafer;
a support unit supporting one surface of the wafer and being movable in a vertical direction; and
a judgment unit to convert the light reflected from the center region of the wafer and detected by the detection unit into a first quantitative measured value, to determine whether the center region of the wafer is faulty by comparing the first measured value with a first reference value, to convert the light reflected from the edge region of the wafer into a second quantitative measured value, and to determine whether the edge region of the wafer is faulty by comparing the second measured value with a second reference value that is different from the first reference value;
wherein the first reference value is calculated as a sum of an average based on previously measured values that have been previously converted into quantitative measured values, respectively, by the judgment unit, and the first measured value, and a product of a standard deviation based on the previously measured values and the first measured value, and a predetermined coefficient;
the second reference value is calculated by adding a predetermined offset value to the first reference value; and
when the first or second measured value escapes from a predetermined range, the judgment unit moves the support unit in the vertical direction so that at least one of the first measured value and the second measured value is within the predetermined range.

* * * * *